ent [19]

United States Patent

Baumoel

[11] 4,232,548
[45] Nov. 11, 1980

[54] LIQUID FLOW METER

[76] Inventor: Joseph Baumoel, 107 Columbia Dr., Jericho, Long Island, N.Y. 11753

[21] Appl. No.: 16,525

[22] Filed: Mar. 1, 1979

[51] Int. Cl.³ .............................................. G01F 1/66
[52] U.S. Cl. .................................. 73/861.28; 73/597; 364/510
[58] Field of Search ...................... 73/194 A, 596, 597, 73/598, 339 A, 24; 364/510, 565, 569

[56] References Cited

U.S. PATENT DOCUMENTS

| 3,869,915 | 3/1975 | Baumoel | 73/194 A |
|---|---|---|---|
| 3,987,674 | 10/1976 | Baumoel | 73/194 A |
| 4,022,058 | 5/1977 | Brown | 73/194 A |
| 4,028,938 | 6/1977 | Eck | 73/194 A |

Primary Examiner—Charles A. Ruehl
Attorney, Agent, or Firm—Ostrolenk, Faber, Gerb & Soffen

[57] ABSTRACT

A sonic flow meter for measuring the rate of flow of a fluid within an enclosed axially elongated hollow conduit is disclosed. First and second transducers are secured to the exterior surface of the conduit. The transducers are spaced from each other along the axis of the conduit such that the first transducer is located downstream from the second transducer with respect to the direction of flow of the fluid. Each of the transducers are adapted to transmit to each other, and receive from each other, sinusoidal sonic signals which pass through the fluid in the conduit. Sonic signal transmission means are provided for causing a plurality of sonic signals to be transmitted in an upstream direction from the first to the second transducer means and for causing an equal plurality of sonic signals to be transmitted in a downstream direction from the second to the first transducer means. Finally, a flow measurement circuit is provided for measuring the rate of flow of the fluid as a function of the difference in time it takes to transmit the sonic signals in the upstream and downstream directions. The flow measurement circuit determines the time difference by measuring the upstream and downstream transmission times with reference to a plurality of zero crossover points of the transmitted sonic signals.

13 Claims, 12 Drawing Figures

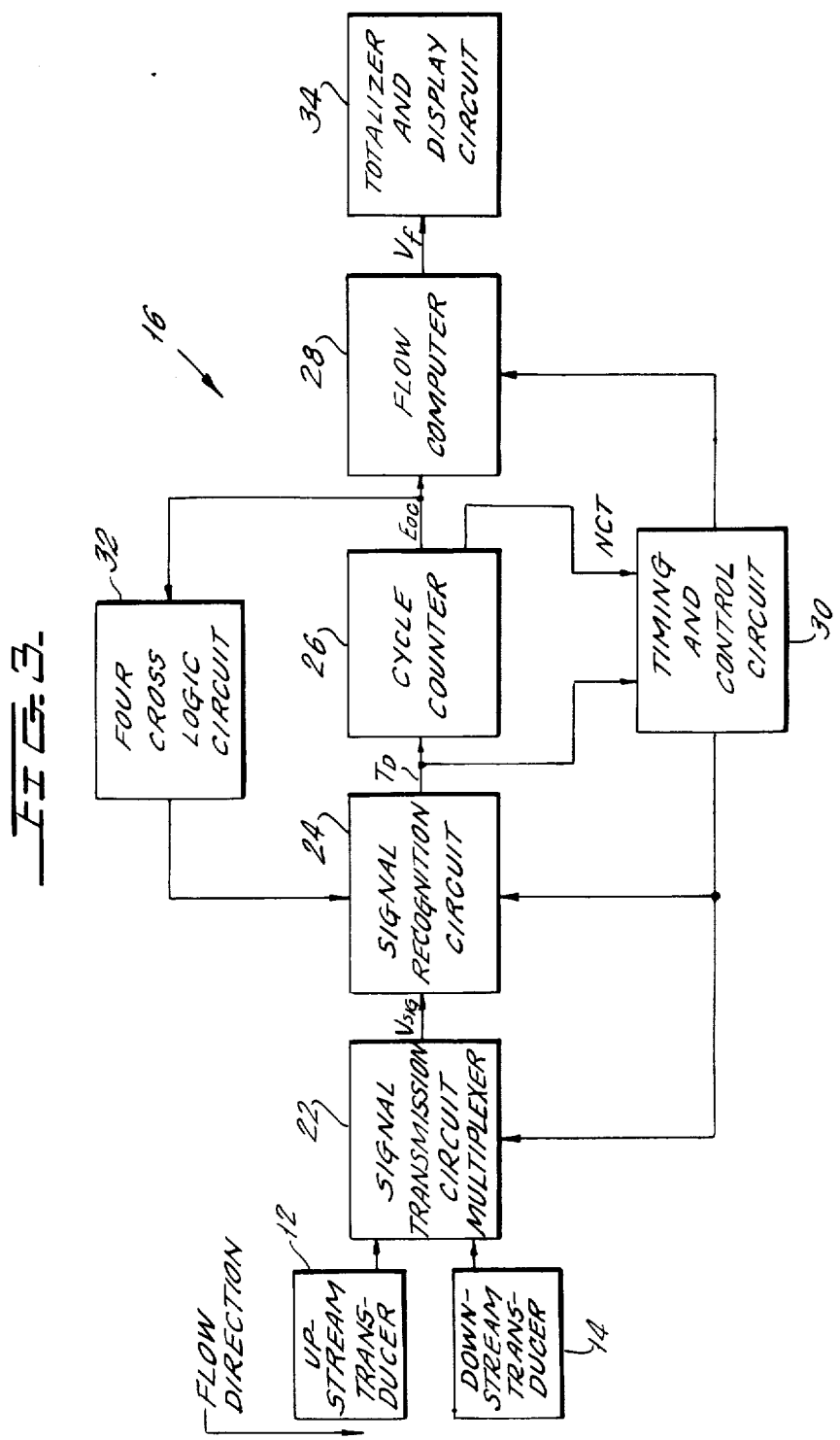

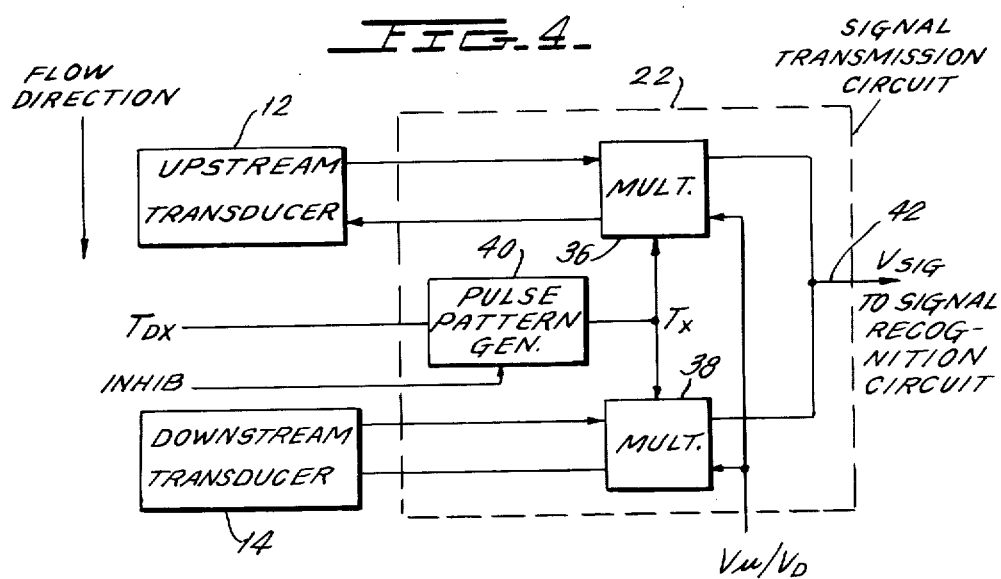
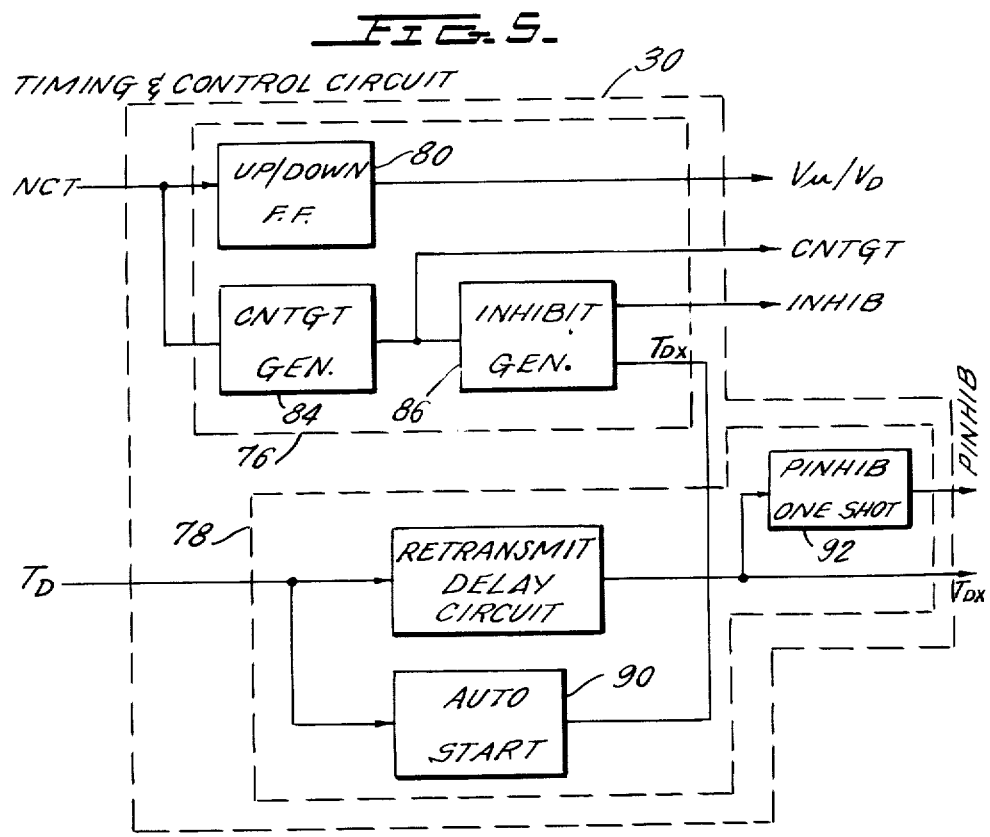

4,232,548

LIQUID FLOW METER

BACKGROUND OF THE INVENTION

The present invention relates to a liquid flow meter, more particularly a sonic liquid flow meter. Liquid flow meters of the foregoing type measure the rate of flow of a liquid within a conduit (e.g., a pipe) by transmitting a plurality of sonic pulses through the fluid in both an upstream and downstream direction and by computing the rate of flow as a function of the difference in time it takes for the upstream beam to travel through the fluid with respect to the time it takes for the downstream beam to flow through the fluid.

Typical of such flow meters are U.S. Pat. Nos. 3,869,915 (hereinafter the '915 patent) and 3,987,674 (hereinafter the '674 patent) both issued to Joseph Baumoel. In accordance with the teachings of these patents, a sonic beam is transmitted between first and second transducers located adjacent the outer walls of the conduit. The transducers are spaced in such a manner that one transducer is located upstream from the other transducer. In each of these patents, a plurality of sonic beams are transmitted from the upstream to the downstream transmitter and then from the downstream to the upstream transmitter. By measuring the difference in travel time of the upstream and downstream pulses, an indication of flow rate of the fluid in the conduit is provided.

The primary advantage of sonic flow meters of the foregoing type is that they do not require an invasion of the conduit walls. As such, installation of the sonic flow system does not require a shutdown of the system being monitored nor does it require the cutting into the conduits. Additionally, since the sonic flow meter does not require physical contact between the measuring apparatus and the liquid whose rate is being measured, there is no possibility that the sonic apparatus will hinder flow or will be adversely affected by the chemical nature of the fluid being monitored.

While sonic flow meters such as those described in the foregoing patents overcome the drawbacks of standard mechanical flow meters, their accuracy depends on their ability to precisely detect the time interval between the instant at which the sonic beam is transmitted from one transducer (e.g., the downstream transducer) until it is received by the second transducer (e.g., the upstream transducer). In practice, at a flow rate of 30 feet per second the difference between the upstream and downstream travel times for a sonic beam is only about 0.2 percent of the time taken to travel either upstream or downstream. Since the travel times are extremely small (approximately 20 microseconds per inch in water) the difference in the upstream and downstream travel time is only a small percentage of the period of the sonic beam being transmitted (which beam is normally a sinusoidal pulse with an exponential envelope in form). In order to obtain the desired accuracy, it is imperative that receipt of the transmitted sonic beam is detected with reference to the same point of the pulse during each upstream-downstream pair of transmissions. In the foregoing patents, this result was obtained by detecting a specific zero crossing point of each of the sinusoidal sonic pulses transmitted.

BRIEF DESCRIPTION OF THE INVENTION

While the foregoing detection procedure has been found to be generally satisfactory, it has been determined that flow readings are affected by systematic noise contained in the fluid container (hereinafter pipe noise). This pipe noise is produced as a result of the ringing of the transmitting transducer as well as other miscellaneous factors. The noise signal is phase coherent with the transmitted sonic beam and can combine with the received liquid signal in a manner which causes a random phase shift of the zero crossover points of the sonic beam if the phase of the pipe noise shifts relative to the liquid signal. This phenomena can best be understood with reference to FIGS. 1A-1D.

FIG. 1A illustrates the wave form of the transmitted sonic pulse as it passes through the liquid in the pipe. As shown therein, this pulse is exponentially sinusoidal in nature, having a frequency determined by the transducer parameters and the excitation signals applied to the transducer. FIG. 1B illustrates a typical wave form of noise contained in the wall of the pipe through which the liquid flows and FIG. 1C illustrates the signal detected by the receiving transducer (for example, the upstream transducer). This signal is a combination of the transmitted sonic beam illustrated in FIG. 1A and the pipe noise illustrated in FIG. 1B. While the magnitude $A_N$ of the pipe noise is fairly small with respect to the magnitude $A_L$ of the transmitted sonic beam, it is sufficiently large to cause phase shifts in the received signal. This phase shift can best be seen in FIG. 1D which illustrates the relative phase of the transmitted sonic beam, the pipe noise and the received signal. As shown therein, the zero cross-over point of the received signal is phase shifted with respect to the transmitted sonic beam due to the pipe noise. Since the frequency and phase of the pipe noise is phase coherent with the signal, its effect on each zero cross-over point of the transmitted sonic pulse will also be systematic, causing a shift of reading as a result of variations in the perceived arrival time of the signal caused by, for example, small changes in liquid velocity, pipe properties, or liquid travel time which might result from changes in temperature or fluid properties. Additionally, since the frequency of the pipe noise is substantially similar to that of the transmitted sonic pulse, it is nearly impossible to filter this noise out of the received signal. As a result, the zero cross-over points of the received signal will exhibit a systematic phase shift which can significantly affect the measurement of the upstream and downstream transmission times.

In order to overcome the foregoing problem, the present invention measures the upstream and downstream transmission times of the transmitted sonic beams at each of a plurality of zero cross-over points (in the example illustrated in FIG. 1A, points A-E). Since the probability that the phase relationship between the pipe noise and the transmitted sonic beam will be identical at each of the zero cross-over points A-E is very small, the average effect of the noise for a large number of upstream and downstream transmissions will be negligible.

BRIEF DESCRIPTION OF THE DRAWINGS

For the purpose of illustrating the invention, there are shown in the drawings several embodiments which are presently preferred; it being understood, however, that this invention is not limited to the precise arrangements and instrumentality shown.

FIG. 3 is a block diagram of the flow measurement circuit of FIG. 2;

FIG. 4 is a block diagram of the signal transmission circuit of FIG. 3;

FIG. 5 is a block diagram of the timing and control circuit of FIG. 3;

DETAILED DESCRIPTION OF THE PREFERRED EMBODIMENT

Figure 2:
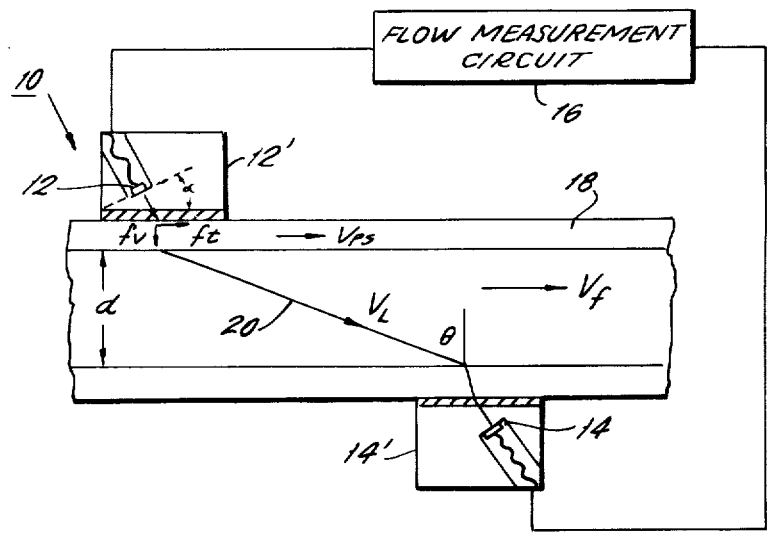
FIG. 2 is a schematic diagram of one embodiment of the liquid flow meter of the present invention.

Referring now to the drawings wherein like numerals indicate like elements, there is shown in FIG. 2 a liquid flow meter constructed in accordance with the principles of the present invention and designated generally as 10. Liquid flow meter 10 includes a pair of transducers 12 and 14 and a flow measurement circuit 16. Transducers 12 and 14 are coupled to the outer wall of pipe 18 by transducer housings 12', 14', respectively, and are selectively energized by flow measurement circuit 16 so as to transmit a plurality of sonic beams in the upstream and downstream directions between transducers 12 and 14. One suitable transducer structure is disclosed in the '674 patent, the disclosure of which is incorporated herein by reference. The transducer disclosed therein establishes a shear mode wave form in the wall of a pipe 18 by selecting the angle α between the face of the transducer 12 and the surface of the outer wall of pipe 18 such that the tangential component $f_t$ of the incident wave in the pipe wall is equal to the velocity $v_{ps}$ of the pipe shear mode vibration characteristic for a pipe 18 of a given wall thickness and material. While it is preferable to utilize a transducer structure which will set up a shear mode vibration in the pipe wall 18, it should be recognized that the present invention is not limited to such a structure and other transducers which do not establish such wave forms may also be utilized without departing from the spirit or scope of the present invention. When a tangential mode wave is not induced in pipe 18, flow equations other than those set forth below must be used. By way of example, those equations set forth in the '915 patent may be utilized. For the purposes of the following description of the invention, it will be assumed that the transducer structure of the '674 patent is utilized.

In addition to selectively enabling transducers 12 and 14, flow measurement circuit 16 measures the difference in travel time of the upstream and downstream pulses generated by transducers 12, 14, respectively. Flow measurement circuit 16 further computes the flow rate $V_f$ of the liquid in pipe 18 as a function of this time differential. In making this computation, flow measurement circuit 16 relies upon the following relationship between the difference in travel time Δ T of the upstream and downstream sonic beams and the velocity of flow $V_f$ of liquid in pipe 18:

$$N\Delta T = K \cdot V_f \cdot T_L \tag{1}$$

wherein $T_L$ is the time that the sonic beam spends in the liquid during its transmission from the transmitting to the receiving transducer; and K is a constant determined by the pipe parameters and the number of transmissions N. The proof for this relationship may be found in the '674 patent.

Solving equation (1) for the flow velocity $V_f$, we get:

$$K \cdot V_f = (\Delta T / T_L) \tag{2}$$

As will be shown below, flow measurement circuit 16 includes apparatus for measuring both ΔT and $T_L$ and for dividing these values to arrive at the flow rate $V_f$.

Referring now to FIG. 3, there is shown a block diagram of a flow measurement circuit 16 constructed in accordance with the principles of the present invention. Flow measurement circuit 16 includes a signal transmission circuit 22, a signal recognition circuit 24, a cycle counter 26, a flow computer 28, a timing and control circuit 30, a four cross logic circuit 32, and a totalizer and display circuit 34. The function of each of these blocks will be described briefly at this point and will be described in some detail below.

In the following description, a transmission sequence in which N sonic pulses are transmitted from upstream transducer 12 to downstream transducer 14 and then N sonic pulses are transmitted from downstream transducer 14 to upstream transducer 12 will be referred to as a "transmission cycle". It should be recognized, however, that this order may be reversed without departing from the spirit and scope of the present invention. In either case, one "transmission cycle" comprises N upstream and N downstream transmissions. Any desired number N can be utilized.

Figure 1:
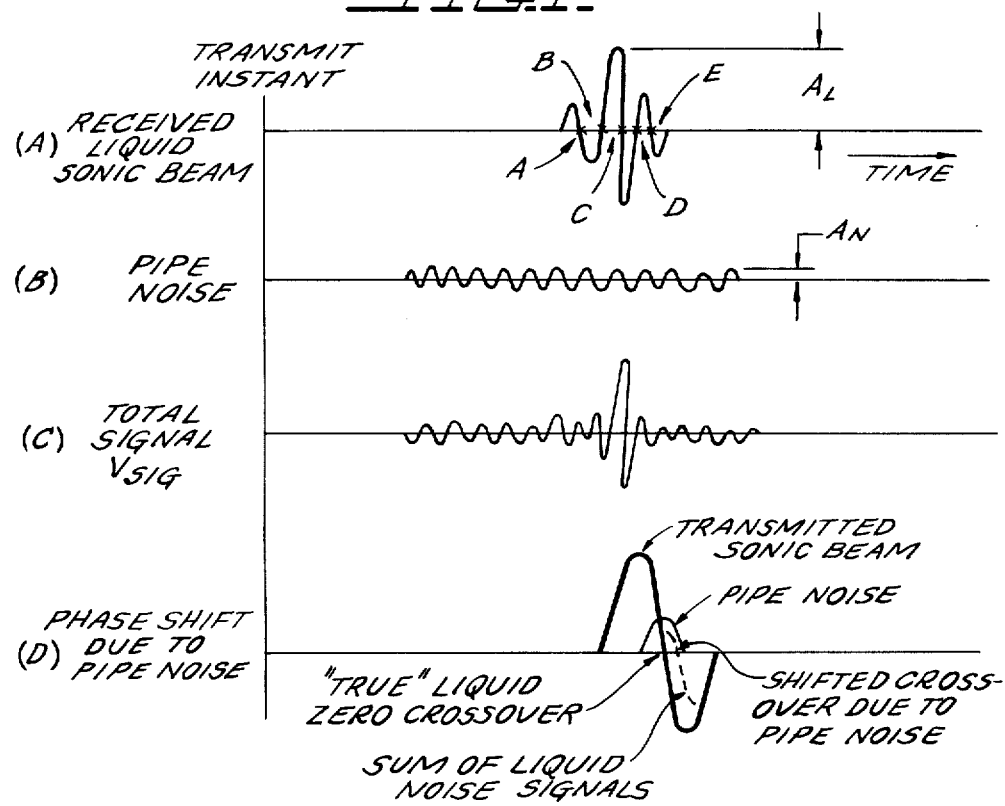
FIG. 1 is a graph showing a plurality of wave forms which demonstrate a phase shift problem overcome by the present invention.

During each transmission cycle, transducers 12 and 14 each receive N transmission pulses from signal transmission circuit 22 at a frequency determined by timing and control circuit 30. Each time a transducer 12, 14 receives a transmission signal from circuit 22, it generates a sonic beam which is transmitted through the liquid in the pipe 18 and is received by the remaining transducer. Receipt of this signal $V_{SIG}$ is detected by signal recognition circuit 24 which identifies receipt of the transmitted sonic beam by detecting a particular one of the zero cross-over points of the received signal $V_{SIG}$ (see FIG. 1A). The particular zero cross-over point which is detected during any given transmission cycle is determined by four cross logic circuit 32 which controls the operation of signal recognition circuit 24 in such a manner that a different zero cross-over point is utilized for each successive transmission cycle. For example, four cross logic circuit 32 may cause signal recognition circuit 24 to detect zero cross over point A during a first transmission cycle, zero cross over point B during a second transmission cycle, zero cross over point C during a third transmission cycle, and zero cross over point D during a fourth transmission cycle. Thereafter, this sequence may be repeated. Generally, any desired sequence of zero cross over points may be utilized as long as the overall effect of averaging the Δ T readings for each transmission cycle is to substantially reduce the effect of noise on the ultimate flow reading of flow detector circuit 10 over a large number of transmission cycles.

Each time signal recognition circuit 24 identifies the zero cross over point selected by logic circuit 32, it generates a recognition signal $T_D$ which is applied to both cycle counter 26 and timing and control circuit 30. Cycle counter 26 counts the number of recognition signals $T_D$ generated by signal recognition circuit 24 and generates output signals NCT and EOC responsive thereto. An output signal NCT is generated whenever N recognition signals $T_D$ have been received by cycle counter 26 and divides each transmission cycle into an upstream and a downstream portion. This signal, in conjunction with recognition signal $T_D$, controls the operation of timing and control circuit 30. During the upstream portion of each cycle, timing and control circuit 30 causes signal transmission circuit 22 to apply a transmit signal to downstream transmitter 14 a predetermined time delay after the generation of recognition signal $T_D$. During the downstream portion of each cycle, timing and control circuit 30 causes signal transmission circuit 22 to apply a transmit signal to upstream transducer 12 a predetermined delay after generation of the recognition signal $T_D$. In both cases, each sonic pulse generated by transducer 12, 14 is generated responsive to recognition of the appropriate zero crossing (as determined by four cross logic 32) by signal recognition circuit 24.

The end of cycle signal EOC generated by cycle counter 26 serves two functions; it causes the output of four cross logic circuit 32 to change at the end of each successive transmission cycle (thereby changing the zero cross-over point detected by signal recognition circuit 24), and it causes flow computer 28 to compute a new flow rate $V_f$ at the end of each transmission cycle.

Flow computer 28 includes circuitry for generating an output voltage $V_f$ proportional to the rate of flow of liquid through pipe 18 in accordance with equation (2), supra. A new signal $V_f$ is generated at the end of each transmission cycle and is applied to totalizer and display circuit 34. Totalizer and display circuit 34 memorizes each successively generated flow signal $V_f$ and averages these readings over a large number of transmission cycles. Totalizer and display circuit 34 converts the average signal into appropriate flow or mass units and displays the same in an appropriate digital or analog display.

Having briefly reviewed the operation of flow measurement circuit 16, the structure and operation of each of the individual elements thereof will now be reviewed in greater detail.

Signal Transmission Circuit

A block diagram of signal transmission circuit 22 is illustrated in FIG. 4. As shown therein, transmission circuit 22 includes a pair of multiplexers 36, 38 and a pulse pattern generator 40. Pulse pattern generator 40 receives enabling pulses $T_{DX}$ from timing and control circuit 30 responsive to generation of a recognition signal $T_D$ by signal recognition circuit 24 (compare FIGS. 6A and 6M). Signal $T_{DX}$ has a pulse width equal to the desired time delay between the generation of the recognition signal $T_D$ and the generation of the next transmission pulse $T_X$. As best shown in FIG. 6B, transmission pulse $T_X$ is preferably a plurality of transmission pulses, the first two of which are in phase with the sine wave generated by transmitting transducer 12 or 14 and the latter of which is out of phase with this signal. While three transmission pulses $T_X$ are preferably generated responsive to each enabling pulse $T_D$, these three pulses will be referred to herein as a single transmission pulse $T_X$.

The transmission pulse $T_X$ generated by pulse pattern generator 40 is applied to the transmitting transducer 12 or 14 via multiplexer 36 or 38, respectively. If flow measurement circuit 16 is in the upstream portion of a given transmission cycle, transmission signal $T_X$ is applied to downstream transducer 14 via multiplexer 38 and transducer 14 acts as the transmitting transducer. In this case, transducer 12 operates as the receiving transducer and the sonic signal $V_{SIG}$ received thereby is applied to the output 42 of signal transmission circuit 22 via multiplexer 36. When flow measurement circuit 16 is in the downstream portion of a given transmission cycle, the transmission pulses $T_X$ are applied to upstream transducer 12 via multiplexer 36 causing transducer 12 to operate as the transmitting transducer. In this case, downstream transducer 14 operates as the receiving transducer and the sonic signal $V_{SIG}$ received thereby is applied to output 42 of signal transmission circuit 22 via multiplexer 38. Control over multiplexers 36 and 38 is determined by the upstream/downstream voltage signal $V_U/V_D$ generated by timing and control circuit 30. By way of example, when this voltage signal is a binary "1" (representing an upstream portion of a transmission cycle), multiplexer 38 applies the transmission signal $T_X$ to transducer 14 and multiplexer 36 applies the sonic signal $V_{SIG}$ received by transducer 12 to the output of signal transmission circuit 22. Conversely, when the upstream/downstream signal $V_U/V_D$ is a binary "0", multiplexer 36 applies the transmit signal $T_X$ to upstream transducer 12 and applies the sonic signal received by transducer 14 to the output of signal transmission circuit 22.

Figure 10:
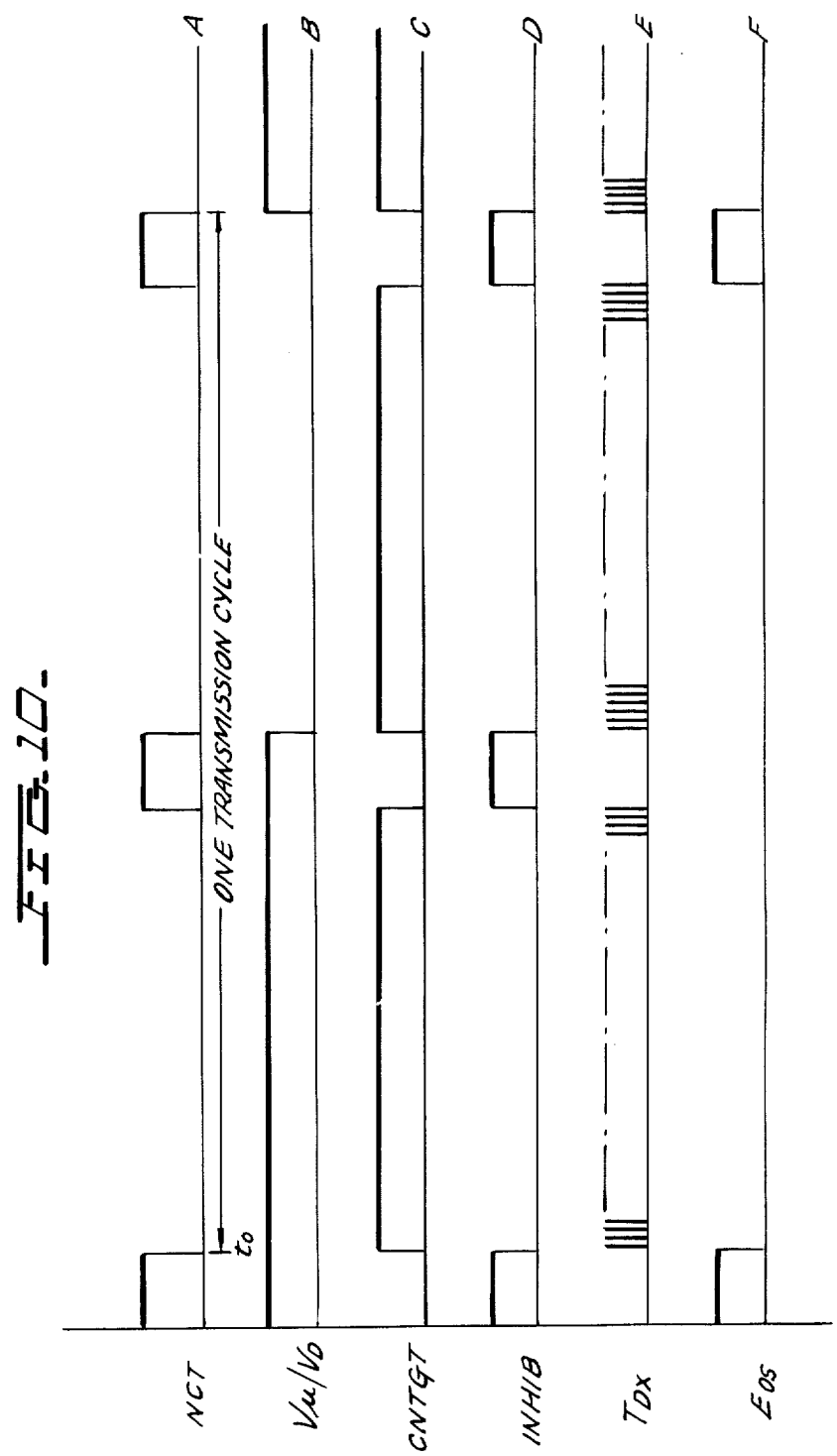
FIG. 10 is a timing diagram for the timing and control circuit of FIG. 5.

Pulse pattern generator 40 also receives an inhibit signal INHIB which is generated by timing and control circuit 30 (FIG. 5). The purpose of this signal is to disable (that is to prevent its turning on) pulse pattern generator 40 during the intervals between transmission cycles during which flow computer 28 computes the flow rate of the liquid within the pipe 18 and during the transition time between upstream and downstream pulsing. The specific function of inhibit signal INHIB will be discussed below with reference to FIG. 10.

Signal Recognition Circuit

Figure 6:
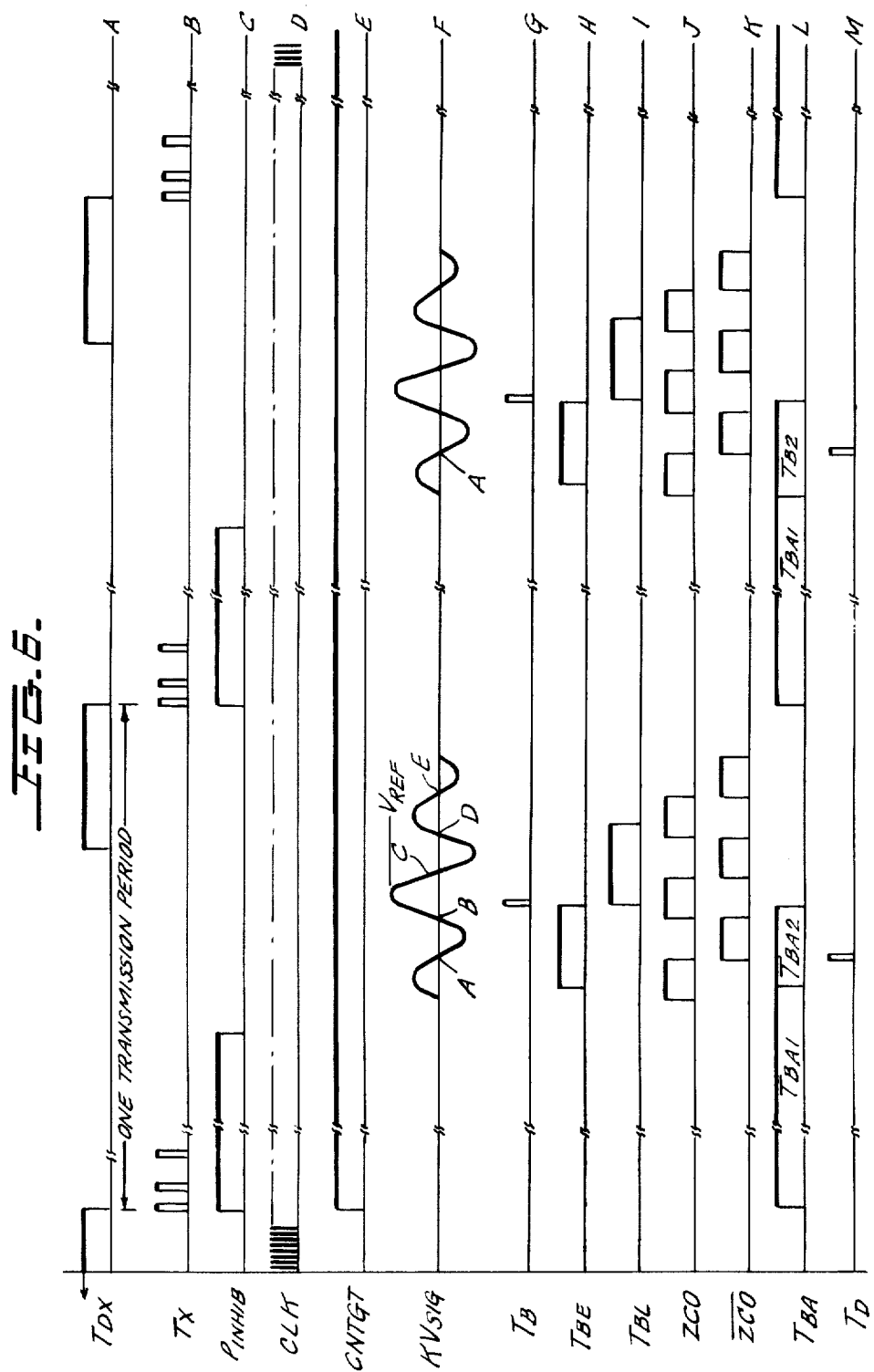
FIG. 6 is a timing diagram for the flow measurement circuit of FIG. 3.
Figure 7:
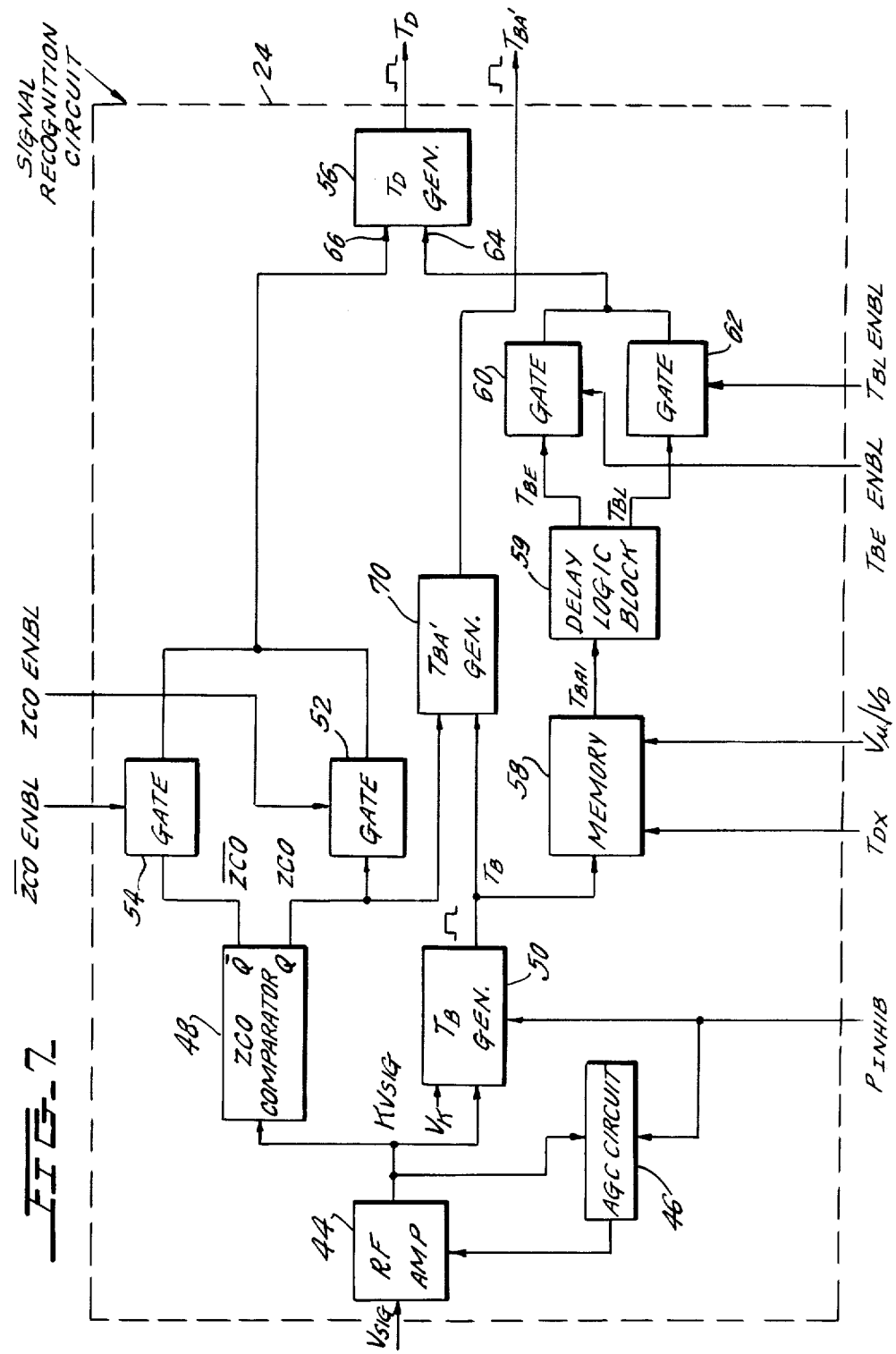
FIG. 7 is a block diagram of the signal recognition circuit of FIG. 3.

A block diagram of signal recognition circuit 24 is shown in FIG. 7. The operation of signal recognition circuit 24 will be described with reference to wave forms of FIG. 6.

The sonic signal $V_{SIG}$ generated by signal transmission circuit 22 is applied to an RF amplifier 44 which normalizes the peak magnitude of the received signal to a predetermined reference value $R_{REF}$ in cooperation with the automatic gain control (AGC) circuit 46. The resultant wave form $KV_{SIG}$ is illustrated in FIG. 6F. While any suitable automatic gain control circuit may be utilized, one such circuit is disclosed in copending application Ser. No. 6183, filed Jan. 24, 1979 in the name of Joseph Baumoel.

The amplified sonic signal $KV_{SIG}$ is applied to the zero crossing comparator 48 and to the $T_B$ generator 50. Zero crossing comparator 48 generates a positive logic output ZCO and a negative logic output $\overline{ZCO}$. The wave forms of these signals are illustrated in FIGS. 6J and 6K, respectively. As shown therein, the outputs of comparator 48 toggle between a binary "1" and a binary "0" responsive to each zero crossing of the normalized wave form $KV_{SIG}$. The two outputs of comparator 48 are applied to gates 52, 54 which also receive a ZCO ENBL and $\overline{ZCO}$ ENBL signals from four cross logic circuit 32 (see FIG. 8). As will be described below, four cross logic circuit 32 only generates one of these enabling signals during each transmission cycle. As such, either output ZCO or $\overline{ZCO}$ is applied to $T_D$ generator 56 during any transmission cycle. In the diagram illustrated in FIG. 6, it is assumed that four cross logic circuit 32 is presently generating the ZCO ENBL signal and that the ZCO output of comparator 48 is applied to $T_D$ generator 56. The significance of this fact will become apparent below.

As mentioned above, the normalized sonic signal $KV_{SIG}$ generated by RF amplifier 44 is also applied to $T_B$ generator 50. $T_B$ generator 50 compares the normalized signal $KV_{SIG}$ with reference voltage $V_{REF}$ and generates a $T_B$ pulse (see FIG. 6G) whenever the magnitude of $KV_{SIG}$ rises above $V_{REF}$. $T_B$ signal generator cooperates with memory 58 to determine the average transmission's time $T_{BA}$ for each sonic signal $V_{SIG}$ transmitted from the transmitting to the receiving transducer as measured between the transmission instant defined by the trailing edge of the $T_{DX}$ signal and the receipt instant defined by the signal $T_B$. Since the exact instant at which the signal $T_B$ is generated will vary as a function of the magnitude of the normalized signal $KV_{SIG}$ (which, in turn, is controlled by the gain of AGC circuit 46), this time is not very precise. Accordingly, the signal $T_B$ is utilized to establish a time zone during which the zero crossing selected by logic circuit 32 should appear. The actual recognition instant will be determined by the appropriate zero crossover point as described below.

The gain determined by automatic gain control circuit 46 will not always be sufficient to normalize the sonic signal to the value $V_{REF}$ due to, for example an instantaneous partial blocking of the sonic beam by air or solids contained in the liquid. As such, the $T_B$ signal will not be generated responsive to some of the transmitted sonic signals. For this reason, it is necessary to memorize the average position of the $T_B$ signal with respect to the transmission signal $T_X$ and to utilize this memorized signal as the basis for determining the location of the sonic signal $V_{SIG}$ and therefore the appropriate zero crossing. To this end, memory 58 memorizes the average transmission time of the last several sonic transmissions as determined by the time delay between the transmission instant identified by the trailing edge of the signal $T_{DX}$ and the reception instant identified by the $T_B$ signal. The $T_{BA}$ signal generated by memory 58 is illustrated in FIG. 6L. As shown therein, the $T_{BA}$ signal has a leading edge corresponding to the transmission instant $T_X$ and a trailing edge corresponding to the average signal reception instant as determined by $T_B$. This trailing edge defines the time zone around which a zero crossing selected by logic circuit 32 should appear. The signal $T_{BA}$ includes first and second portions $T_{BA1}$ and $T_{BA2}$. The second portion, $T_{BA2}$ is of constant duration and is equal in time to one period of the sonic signal $V_{SIG}$. The first portion $T_{BA1}$ is adjusted in length to insure that the entire interval $T_{BA}$ follows the actual transmission time as indicated by the signal $T_B$. The signal $T_{BA1}$ is applied to delay logic block 59 which generates the pules $T_{BE}$ and $T_{BL}$ responsive thereto. As shown in FIGS. 6H and 6I, signals $T_{BE}$ and $T_{BL}$ are equal in length to a single period of the sonic signal $V_{SIG}$ and straddle either side of the end of the signal $T_{BA}$.

Delay logic block 59 may be formed utilizing two cascaded one shots, the first of which receives the signal $T_{BA1}$ and generates the signal $T_{BE}$, the second of which receives the signal $T_{BE}$ and generates the signal $T_{BL}$. The signals $T_{BE}$ and $T_{BL}$ are applied to gates 60, 62, respectively, and represent the early and late zero crossover points with reference to the $T_B$ instant. Gates 60, 62 also receive enabling signals $T_{BE}$ ENBL and $T_{BL}$ ENBL, respectively, from four cross logic circuit 32. Four cross logic circuit 32 generates only one of these enable signals during any given transmission cycle in order that only one of the signals $T_{BE}$ or $T_{BL}$ are applied to $T_D$ generator 56 during any given transmission cycle. In the example illustrated in FIG. 6, it is assumed that the signal $T_{BE}$ ENBL is generated by four cross logic circuit 32 and therefore that signal $T_{BE}$ is applied to $T_D$ generator 56. In this condition, $T_D$ generator 56 receives the $\overline{ZCO}$ signal from gate 54 and the $T_{BE}$ signal from gate 60. $T_D$ generator 56 generates a recognition pulse $T_D$ (see FIG. 6M) whenever a binary "1" is applied to its input 64 and the trailing edge of a positive going pulse is applied to its input 66. Accordingly, the recognition pulse $T_D$ is generated at the zero crossover point A shown in FIG. 6F. During the entire transmission period during which four cross logic circuit 32 generates the output signals ZCO ENBL and $T_{BE}$ ENBL, $T_D$ generator 56 receives the signals ZCO and $T_{BE}$ and generates the recognition signal $T_D$ when the first zero crossover point A of the sonic signal $V_{SIG}$ is detected. During the next succeeding transmission period, four cross logic circuit 32 will change the enabling inputs into signal recognition circuit 24 causing $T_D$ generator 56 to generate the recognition signal $T_D$ responsive to a different zero crossing (e.g., zero crossing B) of the transmitted sonic signal $V_{SIG}$. This phenomena will be discussed in greater detail below.

The signal $T_{BA}'$ is generated by $T_{BA}'$ generator 70 and represents location of the first zero crossing point after the normalized sonic signal $KV_{SIG}$ increases in magnitude above the value $V_{REF}$. The signal $T_{BA}'$ is applied to flow computer 28 and is utilized to compute the time $T_L$ that the sonic beam spends in the liquid during a single transmission from the transmitting to the receiving transducer. The manner in which this computation is made is described hereinafter, and is described in previously referred-to U.S. Pat. No. 3,869,915.

Cycle Counter

Figure 9:
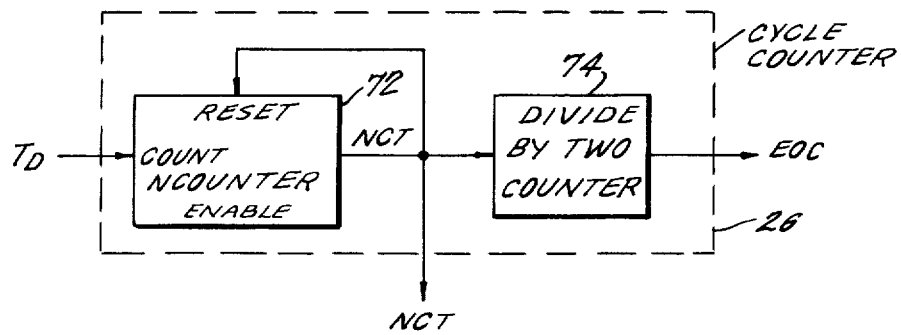
FIG. 9 is a block diagram of the cycle counter of FIG. 3.

Referring to FIG. 9, the recognition signals $T_D$ generated by signal recognition circuit 24 are applied to cycle counter 26, which includes a programmable N counter 72 and a divide-by-two counter 74. The programmable N counter 72 counts the number of recognition signals $T_D$ applied to its count input and generates an output signal NCT whenever it has counted a preprogrammed number N of the recognition signals.

The output signal NCT generated by N counter 72 is applied to its reset input in order to reset the N counter 72 to zero at the end of each upstream or downstream transmission period. Alternatively, the count in N counter 72 may be reset to the predetermined value N and the count in counter 72 may be counted down to zero responsive to the recognition signals $T_D$ in order to generate the output signal NCT. The output signal NCT is applied to the divide-by-two counter 74 which generates an end-of-cycle signal EOC responsive to every other NCT signal. This signal indicates the end of each transmission cycle.

Timing and Control Circuit

A block diagram of timing and control circuit 30 is illustrated in FIG. 5. As shown therein, timing and control circuit 30 includes a transmission cycle control section 76 and a transmission signal control section 78. Transmission cycle control section 76 receives the output pulses NCT generated by cycle counter 26 and generates the output signals which define the upstream and downstream portions of each of the transmission cycles. Particularly, transmission cycle control section 76 generates the upstream/downstream control voltage $V_U/V_D$, the count-gate signal CNTGT and the inhibit signal INHIB (see FIG. 10).

Each NCT signal generated by cycle counter 26 is applied to upstream/downstream flip-flop 80 whose output toggles between a binary "1" and a binary "0" responsive to the negative edge of each NCT signal. The upstream/downstream signal $V_U/V_D$ is applied to multiplexers 36, 38 of signal transmission circuit 22 in order to insure that the transmission pulses are applied to the appropriate transducer 12, 14. The upstream/downstream signal $V_U/V_D$ is also applied to the up/down input of a CNTGT counter 82 (FIG. 12) located in flow computer 28 (FIG. 3). As will be described in further detail below, counter 82 determines the time differential between the upstream and downstream transmission times. Each NCT signal is also applied to count-gate generator 84 (FIG. 5) which generates a count-gate signal CNTGT (see FIG. 10C). As shown therein, the CNTGT signal is preferably the inverse of the NCT signal.

Count gate signal CNTGT is applied to inhibit generator 86 which generates an inhibit signal INHIB (see FIG. 10D) which is applied to pulse pattern generator 40 (FIG. 4) to disable pulse pattern generator 40 at the end of each upstream and downstream portion of each transmission cycle.

The transmission control section 78 of timing and control circuit 30 controls the transmission instant of each successive sonic signal $V_{SIG}$ as a function of the $T_D$ signal generated by signal recognition circuit 24.

As shown in FIG. 5, transmission signal control section 78 of timing and control circuit 30 includes a retransmit delay circuit 88, an auto start circuit 90, and a $P_{INHIB}$ one shot 92. Retransmit delay circuit 88 receives the $T_D$ pulse generated by signal recognition circuit 24 and generates an enabling pulse $T_{DX}$ a predetermined time period after receipt of the $T_D$ signal. The purpose of auto start circuit 90 is to insure that a sonic pulse is transmitted should no pulse be recognized for some given length of time.

Enabling signal $T_{DX}$ is applied to both pulse pattern generator 40 (as described above), and $P_{INHIB}$ one shot 92. $P_{INHIB}$ one shot 92 generates the $P_{INHIB}$ signal responsive thereto and applies this signal to AGC circuit 46 and $T_B$ generator 50.

Four Cross Logic Circuit 32

Figure 8:
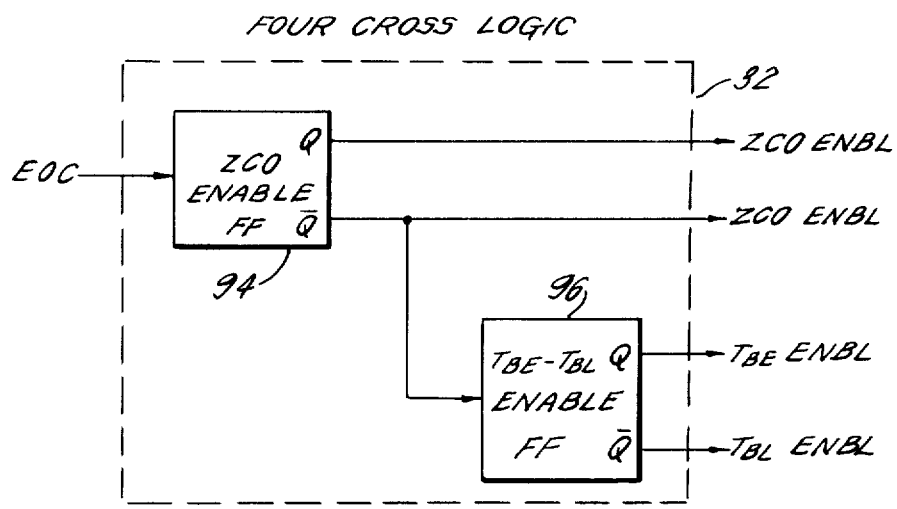
FIG. 8 is a block diagram of the four cross logic circuit of FIG. 3.
Figure 11:
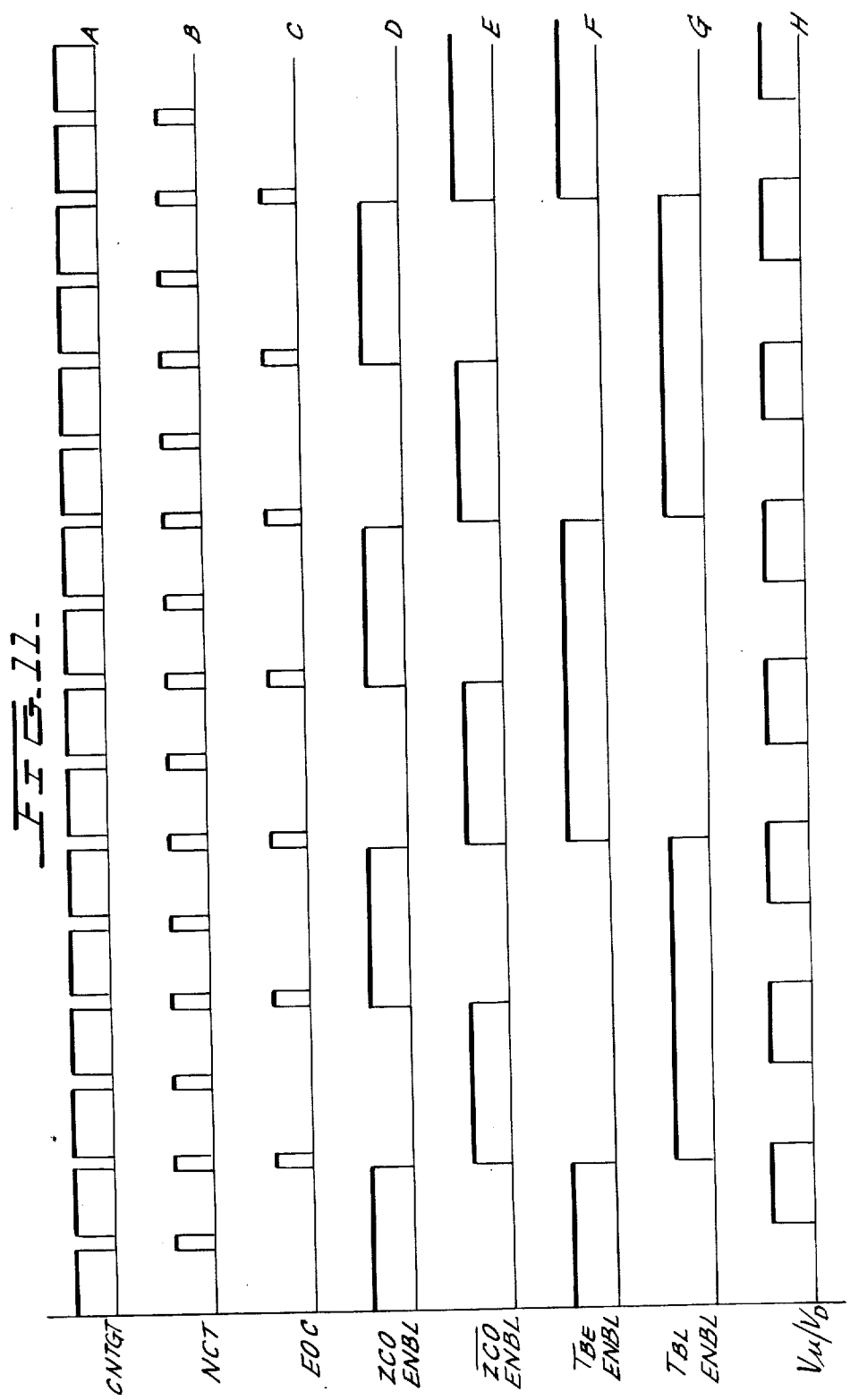
FIG. 11 is a timing diagram for the four cross logic circuit of FIG. 8.

One possible four cross logic circuit 32 is illustrated in FIG. 8. As shown therein, four cross logic circuit 32 includes a ZCO enable flip-flop 94 and a $T_{BE}$-$T_{BL}$ enable flip-flop 96. ZCO enable flip-flop 94 receives the end of cycle signal EOC and toggles its Q and $\bar{Q}$ outputs responsive to a leading edge of each end-of-cycle signal EOC. The form of the ZCO ENBL and $\overline{ZCO}$ ENBL outputs is illustrated in FIGS. 11D and 11E, respectively. As shown therein, only one of the two outputs will be at a binary "1" level during any given transmission period. The $\bar{Q}$ output of flip-flop 94 is applied to the input of flip-flop 96 whose Q and $\bar{Q}$ outputs toggle responsive thereto. The resulting $T_{BE}$ ENBL and $T_{BL}$ ENBL outputs are illustrated in FIGS. 11F and 11G, respectively. Again, only one of these outputs will be at a binary "1" level during any given transmission period. Using the particular sequence of enabling signals illustrated in FIGS. 11D-11G, four cross logic circuit 32 causes signal recognition circuit 24 to recognize the zero crossing points A, D, C, and B in successive transmission cycles. The sequence repeats every fourth transmission cycle.

While four cross logic circuit 32 has been shown utilizing a pair of flip-flops, it should be recognized that any logic circuit 32 may be utilized as long as it generates output signals which have the effect of causing signal recognition circuit 24 to recognize a different zero crossover point during each successive transmission cycle. The particular order in which the zero crossover points are recognized may be selected as desired as long as the overall effect of utilizing the different zero crossover points is to average out the effect of noise on the received signal.

In the above-described embodiment of the present invention, transmission time measurements are made with reference to four cross-over points (i.e., A, B, C, D). Additionally, each cross-over point is utilized with the same frequency (i.e., one in four). While such a system will favorably compensate for the effects of noise on the flow meter, improved results may be obtained by utilizing a greater number of crossover points (e.g., A, B, C, D and E) and by utilizing those crossover points which are least affected by noise at a greater frequency than the remaining crossover points. Referring to FIG. 6F, it can be seen that cross-over points B, C and D are associated with the peak magnitude cycle of the received signal $V_{SIG}$. Since this cycle has the greatest magnitude (i.e., $V_{SIG} \approx V_{REF}$), it is least affected by pipe noise and the phase shift of the zero cross-over points B, C and D is less than that of the remaining cross-over points (e.g., A, E). By utilizing cross-over points B, C and D at a greater frequency (e.g., twice as often) than the remaining cross-over points, it is possible to improve the measurement accuracy of the flow meter.

In accordance with one possible modification of the circuit described above, $T_B$ generator 50 may be modified to generate a negative peak signal $T_{BN}$ corresponding to the negative peak of the received signal $V_{SIG}$ in addition to the positive peak signal $T_B$. Referring to FIGS. 6F and 6G, the illustrated $T_B$ signal would be designated the positive peak signal $T_{BP}$ and a negative peak signal $T_{BN}$ would be generated in the area of the crest of the wave form between points C and D (specifically at the point the received wave form falls below some negative reference voltage. Memory 58 would also be modified to memorize the time of occurrence of $T_{BN}$ as well as the time of occurrence of $T_{BP}$. During the appropriate transmission cycles, the memorized signal $T_{BA1}$ associated with the memorized negative peak signal $T_{BN}$ would be applied to delay logic block 59 so as to generate early and late peak signals $T_{BEN}$ and $T_{BLN}$, respectively. These latter signals would be identical to the signals $T_{BE}$ and $T_{BL}$, respectively, illustrated in FIGS. 6H and 6I, but would straddle either side of the negative peak signal $T_{BN}$. As such, these signals would be shifted over to the negative peak of the received wave form lying between points C and D. Finally, four cross logic circuit 32 would be modified to generate a positive peak control signal POSPK during four successive transmission cycles followed by a negative peak control signal $\overline{POSPK}$ during the next four transmission cycles. The signal would be applied to $T_B$ generator 50 and to memory 58 and would inform the $T_B$ generator 50 whether to generate the positive or negative peak signal $T_{BP}$ or $T_{BN}$ during any given transmission cycle. This signal would also inform the memory 58 whether to utilize the memorized $T_{BA}$ signal associated with the positive peak or the negative peak.

Flow Computer

Figure 12:
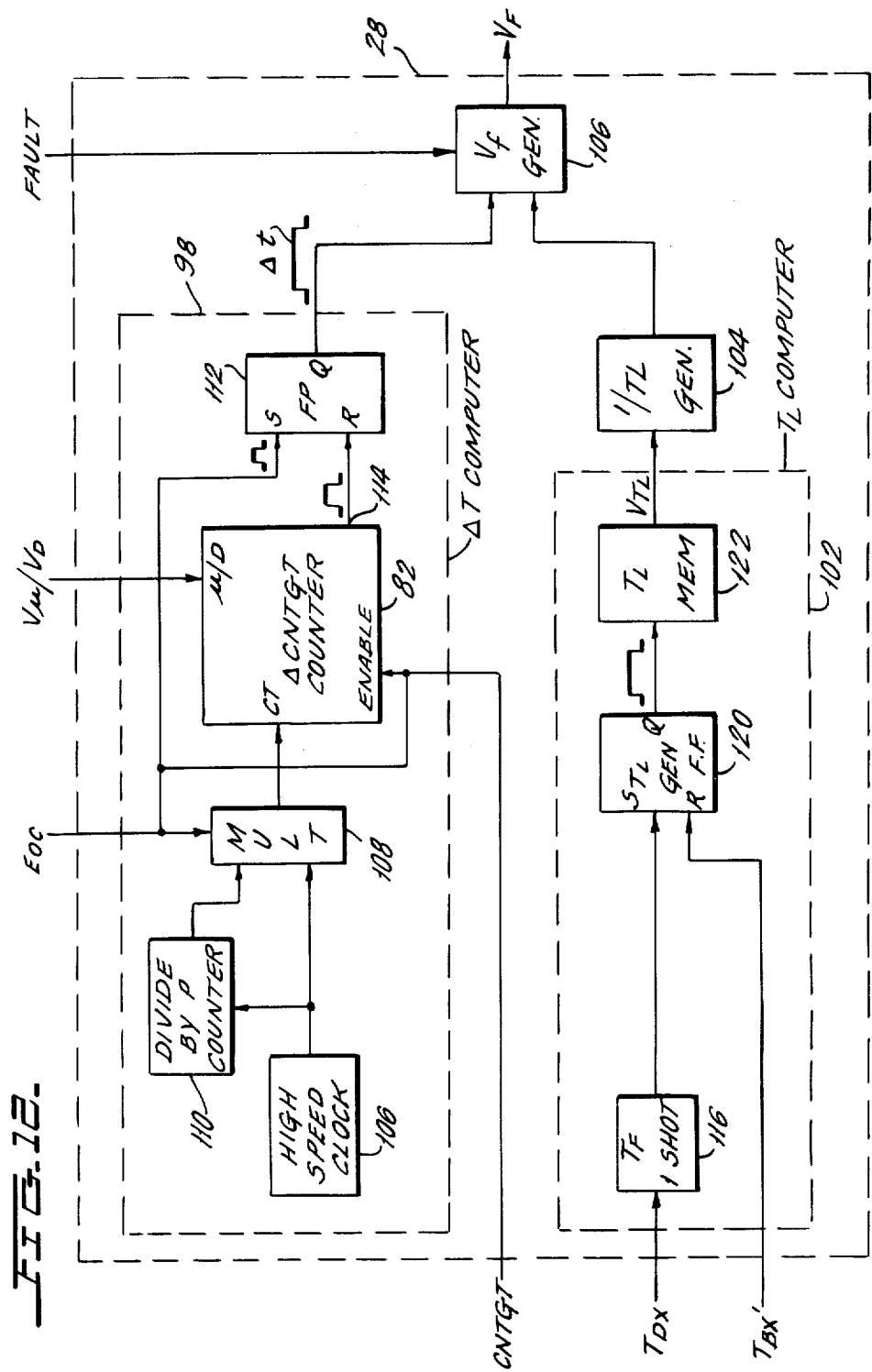
FIG. 12 is a block diagram of the flow computer of FIG. 3.

The preferred structure of flow computer 28 is illustrated in FIG. 12. As shown therein, flow computer 28 includes a $\Delta T$ computer 98, a $T_L$ computer 102, a $1/T_L$ generator 104 and a $V_f$ generator 106. The primary component of $\Delta T$ computer 98 is $\Delta CNTGT$ counter 82. $\Delta CNTGT$ counter 82 determines the time differential between the upstream and downstream transmission times of the sonic signals transmitted during a single transmission cycle. To this end, the count in counter 82 is increased by a high speed clock 106 during the upstream transmission portion of each transmission cycle thereafter counted down by the high speed clock 106 during the downstream portion of each transmission cycle. The residue count in counter 82 at the end of the complete transmission cycle is representative of the time differential between the upstream and downstream transmission times and is utilized to generate an output pulse whose duration is proportional to that time differential.

High speed clock 106 generates a high frequency pulse train and applies this pulse train to both multiplexer 108 and divide by P counter 110. Whenever the end-of-count signal EOC is a binary "0" multiplexer 108 applies the output of high speed clock 106 to the count input of counter 82. Whenever the end-of-count signal EOC is a binary "1" multiplexer 108 applies the output of counter 110 to the count input of counter 82.

Counter 82 counts up, at a rate determined by clock 106 during the upstream portion of each transmission cycle and counts down at this rate during the downstream portion thereof. The exact counting intervals are defined by the two count gate signals CNTGT applied to the enable input of counter 82. Since the length of the upstream CNTGT signal will be greater than the length of the downstream CNTGT signal (due to the rate of flow of the liquid in pipe 16), the end of the downstream transmission portion of each transmission cycle is representative of the difference in the upstream and downstream transmission times. This residue count is converted into a pulse $\Delta T$ whose width is proportional to the difference in transmission times by counting counter 82 down to zero at a frequency determined by the output of divide by P counter 110. Particularly, the end of cycle signal EOC is applied both to multiplexer 108 and to the enable input of counter 82 causing the multiplexer 108 to apply the output of counter 110 to the count input of counter 82 and causing counter 82 to count down at the rate determined by the output of counter 110 to zero.

The end of cycle signal EOC is also applied to the set input of flip-flop 112. The positive edge of the EOC signal causes the Q output of flip-flop 112 to toggle to a binary "1" level. Once the count in counter 82 has counted down from its residue level to zero, it generates a short pulse at its output 114, which is applied to the reset input of flip-flop 112 and causes the Q output of flip-flop 112 to toggle to a binary "0" level. As a result, flip-flop 112 generates an output pulse whose width is proportional to the difference in the upstream and downstream transmission times $\Delta T$.

As shown in equation (2), supra, the flow rate $V_f$ is computed by dividing the difference in upstream and downstream transmission times $\Delta T$ by the time $T_L$ which each sonic beam transmitted between transducers 12, 14 spends in the liquid in pipe 18. In order to perform this computation, flow computer 28 includes a $T_L$ generator 102. As set forth in the '915 patent, the time $T_L$ which the sonic signal spends in the liquid varies with varying liquid temperatures and densities. Accordingly, some means must be provided for continually updating the value of the time $T_L$.

When traveling between transducers 12 and 14, the sonic beam pulse travels through the transducer housings 12', 14', through the wall of pipe 18, and through the liquid in the pipe. The total time $T_T$ is the time between the instant the transmission pulse $T_X$ is applied to the transmitting transducer and the instant (as determined by the signal $T_{BA}'$) at which the peak of the transmitted pulse is recognized by the flow measuring circuit. Accordingly, the time $T_T$ is equal to the time the sonic pulse spends in the liquid ($T_L$) plus a fixed time $T_F$ which includes the time the sonic beam spends in the walls of pipe 18, the time the sonic beam spends in the transducer housings 12', 14' and certain electronic delay times between the instant at which the transmit signal $T_X$ is applied to the transducer and the instant the sonic beam is actually recognized by the measuring circuit. The foregoing relationship may be expressed mathematically as follows:

$$T_T = T_F + T_L \qquad (3)$$

Solving the foregoing equation for the time in the liquid $T_L$ we get:

$$T_L = T_T - T_F \qquad (4)$$

$T_L$ computer 102 relies upon the foregoing relationship to compute the time in the liquid $T_L$. Particularly, $T_L$ computer 102 measures the total time difference between the generation of the transmit pulse $T_X$ (as defined by the trailing edge of the enabling pulse $T_{DX}$) and the instant at which the sonic signal is recognized by the measuring circuit (as defined by the $T_{BA}'$ signal) and subtracts the fixed time delay $T_F$ therefrom.

Referring again to FIG. 12, $T_L$ computer 102 includes a fixed time delay one shot 116 which receives the enabling signal $T_{DX}$ and generates a pulse of a fixed duration (equal in length to the fixed time delay $T_F$) responsive to the trailing edge thereof. The $T_F$ pulse generated by one shot 116 is applied to the set input of $T_L$ generator flip-flop 120 causing the Q output thereof to toggle to a binary "1" level. The output remains at this level until the $T_{BA}'$ signal is applied to the reset input of flip-flop 120 at which point the output of flip-flop 120 toggles to a binary "0" level. As a result, flip-flop 120 generates an output pulse whose width is proportional to the time in the liquid $T_L$. $T_L$ memory 122 may be a capacitor which generates an output voltage $V_{TL}$ which is representative of the time in the liquid $T_L$.

As noted above, the difference in transmission time $\Delta T$ must be divided by the time in the liquid $T_L$ to arrive at the flow rate $V_f$. In order to obtain this relationship, the signal generated by $T_L$ computer 102 is applied to a $1/T_L$ generator 104 which generates an output signal whose magnitude is proportional to $1/T_L$. The outputs of $\Delta T$ computer 98 and $1/T_L$ generator 104 are applied to $V_f$ generator 100 which effectively multiplies these two signals to arrive at the flow signal $V_f$. By way of example, $V_f$ generator 106 may include a capacitor which is charged by a current generated by $1/T_L$ generator 104 for a time period determined by the pulse generated by $\Delta T$ computer 98.

Totalizer and Display Circuit

Totalizer and display circuit 34 memorizes each successive generated flow signal $V_f$ and averages these readings over a large number of transmission cycles. By way of example, the flow signals $V_f$ generated by flow computer 28 may be averaged for a total period of four seconds at the end of which an average flow signal output is generated. This signal may be converted into any appropriate flow or mass units and displayed in an appropriate digital or analog display.

It should be noted that while the process and apparatus of the invention have been described with reference to sonic measurement equipment and sonic pulses that the invention has broader application and could be used with electrical signals and circuits.

The present invention may be embodied in other specific forms without departing from the spirit or essential attributes thereof and, accordingly, reference should be made to the appended claims, rather than to the foregoing specification as indicating the scope of the invention.

What is claimed is:

1. A sonic flow meter for measuring the rate of flow of a fluid within an enclosed axially elongated hollow conduit, comprising:

first and second transducer means secured to the exterior surface of said conduit; said first and second transducer means being spaced from each other along the axis of said conduit such that said first transducer means is located downstream from said second transducer means with respect to the direction of flow of said fluid; each of said transducer means being adapted to transmit to each other, and to receive from each other, sinusoidal sonic signals which pass through said fluid in said conduit;

sonic signal transmission means for causing said first transducer means to transmit N sonic signals in an upstream direction from said first to said second transducer means and for causing said second transducer means to transmit N sonic signals in a downstream direction from said second to said first transducer means during each of a plurality of successive transmission cycles; and flow measurement circuit means for measuring the rate of flow of said fluid as a function of the difference in time it takes to transmit said sonic signals in said upstream and said downstream directions, said flow measurement circuit means determining said time difference by measuring said upstream and downstream transmission times with reference to a single zero cross-over point of each of said received sonic signals, the particular zero cross-over point referenced during any given transmission cycle being the same for each sonic signal received in that transmission cycle, the particular zero cross-over point referenced during each successive transmission cycle being different than the zero cross-over point referenced during a prior transmission cycle.

2. The sonic flow meter of claim 1, wherein:

said flow measurement circuit means determines the difference between said upstream and downstream transmission times at the end of each of said transmission cycles; and said flow measurement circuit means measures said rate of flow by averaging said difference between said upstream and downstream transmission times over a plurality of said transmission cycles.

3. The sonic flow meter of claim 2, wherein the location of said plurality of zero cross-over points is affected by noise associated with said conduit, the location of some of said zero cross-over points being affected by said noise to a lesser degree than the remaining zero cross-over points, and wherein said flow measurement circuit means determines said difference between said upstream and downstream transmission times with respect to those zero cross-over points whose location is affected by said noise to said lesser degree at a greater frequency than the remaining said zero cross-over points.

4. The sonic flow meter of claim 2, wherein said flow measurement circuit means comprises:

signal recognition circuit means for generating a recognition signal upon receipt of a transmitted sonic signal by either of said transducer means, said signal recognition circuit generating said recognition signal responsive to the detection of one of said plurality of zero cross-over points;

zero cross-over logic means for causing said signal recognition circuit to generate said recognition signal responsive to the detection of a different one of said plurality of zero cross-over points during each successive said transmission cycle, said zero cross-over logic means also for causing said signal recognition circuit to generate said recognition signal responsive to the detection of the same zero cross-over point during any given transmission cycle;

flow computer means for generating a flow signal indicative of the rate of flow of said fluid in said conduit at the end of each of said transmission cycles whereby each of said flow signals is associated with a different said transmission cycle, said flow computer means generating said flow signal as a function of the difference in time it takes to transmit said sonic signals in said upstream and said downstream directions as indicated by said recognition signal in the transmission cycle associated therewith; and means for computing an average rate of flow of said fluid in said conduit as a function of a plurality of said flow signals.

5. The sonic flow meter of claim 4, wherein said flow measurement circuit means further includes display means for displaying said average flow rate.

6. The sonic flow meter of claim 4, wherein said flow computer means computes said flow rate in accordance with the following equation:

$$V_f = (K \Delta T)/T_L$$

wherein $V_f$ is a signal indicating the rate of flow of said fluid through said conduit, K is a proportionality constant, $\Delta T$ is the difference in the upstream and downstream transmission times and $T_L$ is the time the sonic signal spends in the fluid during a single transmission between said first and second transducer means.

7. A method for measuring the arrival time of a repetitive sinusoidal wave form pulse which is accompanied by noise; said method comprising the steps of: repetitively detecting the occurrence of a plurality of zero cross-over points of said wave form, averaging the time of arrival of each said cross-over points within said wave form to determine the arrival time for each such cross-over without the effect of the presence of noise.

8. A method for measuring the rate of flow of a fluid within an enclosed axially elongated hollow conduit, comprising the steps of:
   securing first and second transducer means to the exterior surface of said conduit such that said first and second transducer means are spaced from each other along the axis of said conduit, said first transducer means being located downstream from said second transducer means with respect to the direction of flow of said fluid;
   transmitting N sonic signals in an upstream direction from said first transducer means to said second transducer means and transmitting N sonic signals in a downstream direction from said second to said first transducer means during each of a plurality of transmission cycles, each of said sonic signals having a plurality of zero cross-over points; and
   measuring the rate of flow of said fluid by determining the difference in time it takes to transmit said sonic signals in said upstream and said downstream directions, said step of determining said time difference including the step of measuring said upstream and downstream transmission times with reference to a single said zero cross-over point of each of said received sonic signals, the particular zero cross-over point referenced during any given transmission cycle being the same for each sonic signal received in that transmission cycle, the particular zero cross-over point referenced during each successive transmission cycle being different than the zero cross-over point referenced during a prior transmission cycle.

9. The method of claim 8, wherein said step of determining the difference between said upstream and downstream transmission times includes the step of making such determination at the end of each said transmission cycle.

10. The method of claim 9, wherein said step of measuring the rate of flow of said fluid includes the step of averaging the determinations of said differences between said upstream and downstream transmission times over a plurality of said transmission cycles.

11. The method of claim 10, wherein the location of said plurality of zero cross-over points is affected by noise associated with said conduit, the location of some of said zero cross-over points being affected by said noise to a lesser degree than the remaining said zero cross-over points, and wherein said difference between said upstream and downstream transmission times is measured with respect to those zero cross-over points whose location is affected by said noise to said lesser degree at a greater frequency than the remaining said zero cross-over points.

12. The method of claim 11, wherein said flow rate is computed in accordance with the following equation:

$$V_f = (K \Delta T)/T_L$$

wherein $V_f$ is a signal indicating the rate of flow of said fluid through said conduit, K is a proportionality constant, $\Delta T$ is the difference in the upstream and downstream transmission times and $T_L$ is the time the sonic signal spends in the fluid during a single transmission between said first and second transducer means.

13. Apparatus including means responsive to the receipt of a repetitive sinusoidal pulse signal; said apparatus including means for measuring the arrival time of repetitive sinusoidal waveform pulses which are accompanied by noise, means for detecting the zero cross-over point of each of a plurality of loops in said sinusoidal waveform pulse, means averaging the time of arrival of each of the corresponding zero cross-over points in each repetitively received signal, and means connecting a signal related to the averaged time of arrival of at least a selected one of said zero cross-over points to said means responsive to said signal.

* * * * *